United States Patent [19]

Matsumoto et al.

[11] Patent Number: 5,500,445
[45] Date of Patent: Mar. 19, 1996

[54] INTRAOCULAR IRRIGATING AND ENUCLEATED EYEBALL PRESERVATIVE COMPOSITION

[75] Inventors: Takahiro Matsumoto, Akashi; Shogo Sameshima; Kenichi Yoshida, both of Kobe, all of Japan

[73] Assignee: Senju Pharmaceutical Co., Ltd., Osaka, Japan

[21] Appl. No.: 197,325

[22] Filed: Feb. 16, 1994

[30] Foreign Application Priority Data

Feb. 22, 1993 [JP] Japan .................................. 5-31650
Apr. 26, 1993 [JP] Japan .................................. 5-99416

[51] Int. Cl.$^6$ ............................................. A61K 31/34
[52] U.S. Cl. .................................. 514/474; 514/912
[58] Field of Search ............................ 514/75, 77, 474, 514/912

[56] References Cited

U.S. PATENT DOCUMENTS 5,194,445 3/1993 Satoh et al. .......................... 514/474

OTHER PUBLICATIONS

The Merck Index, Eleventh Edition, 1989, pp. 130–131.
Chemical Abstracts 111:45280t (1989). Senoo et al.

*Primary Examiner*—Zohreh Fay
*Attorney, Agent, or Firm*—Wenderoth, Lind & Ponack

[57] ABSTRACT

This invention relates to an intraocular irrigating and enucleated eyeball preservative composition containing a phosphoric acid diester compound of the following formula or a pharmacologically acceptable salt thereof

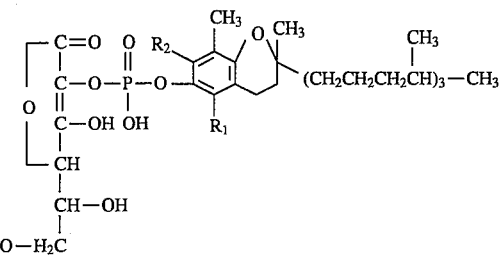

wherein $R_1$ and $R_2$ are the same or different and each represents a hydrogen atom or a methyl group.

The composition of this invention is highly lenient to the ocular tissues, particularly in the sense that it protects the corneal (endothelial) cells which are most susceptible to physiological damage in ophthalmic surgery, with the result that various ophthalmic operations can be carried out with sufficient safety. Furthermore, since the composition of this invention may help retain the physiological functions of the enucleated eyeball without injuring its tissues, it can be used with advantage for the preservation of the cornea, retina, crystalline lens and so on.

4 Claims, 1 Drawing Sheet

INTRAOCULAR IRRIGATING AND ENUCLEATED EYEBALL PRESERVATIVE COMPOSITION

BACKGROUND OF THE INVENTION

1. Field of the Invention

This invention relates to a useful intraocular irrigating and enucleated eyeball preservative composition. More particularly, this invention relates to a useful intraocular irrigating and enucleated eyeball preservative composition containing an ascorbyl tocopheryl phosphate compound or a pharmacologically acceptable salt thereof.

2. Description of the Prior Art

With the recent progress and spread of ophthalmic surgery, inclusive of cataract surgery and operations for transplantation of the cornea, iris or vitreous body, there is a great need for satisfactory intraocular irrigating solutions for protecting the intraocular tissues in such operative procedures. If only inadequate provisions are available for the protection of intraocular tissues in ophthalmic operations and the tissues sustain physiological damage, the postoperative courses will be unfavorable with corneal opacity, glaucoma and retinitis ensuing at times. As the intraocular irrigating solution, one close to physiologic aqueous in composition is of course preferred but generally, so far, physiological saline, lactated Ringer's solution, BSS (Balanced Salt Solution) (trade name) and BSS PLUS (trade name) have been mostly employed for intraocular irrigation. However, these intraocular irrigating solutions are not effective enough to protect corneal (endothelial) cells which are most liable to sustain physiological damage in ophthalmic operations. Under the circumstances, the development of intraocular irrigating solutions with an improved functionality to protect the intraocular tissues, particularly corneal (endothelial) cells, has been awaited in earnest.

Meanwhile, in an operation for the implantation of an ocular tissue graft such as the cornea, retina or crystalline lens, the ocular tissue graft material isolated from a donor must be preserved in such a manner that it may retain its physiological function until it has been ultimately transplanted in a recipient. A number of enucleated eyeball preservatives have heretofore been proposed for upholding the physiological competence of enucleated globes but their efficacies insure a preservation period only about 2 weeks at most. For example, in Japan a glucose phosphate Ringer's solution containing 3.5% of dextran is in common use as a globe preservative today but the dextran (DX) penetrates into the cornea (epithelium, stroma and endothelium) in an early stage of preservation (within a few days) to draw in water into the tissues and reportedly induce marked corneal swelling. Moreover, it is reported that dextran weakens the joint between the corneal endothelium and Descemet's membrane to cause a hypofunction of endothelial cells. Accordingly, enucleated eyeball preservatives, typically those containing chondroitin sulfate (CS) instead of dextran, are being explored for development but none have overcome the above-mentioned disadvantages. After all, there is no eyeball preservative available today that is fully satisfactory.

Under the circumstances described above, the inventors of this invention explored the efficacies of ascorbyl tocopheryl phosphate compounds and their pharmacologically acceptable salts and discovered that these compounds have an excellent intraocular tissue-protecting action. Starting from the finding, the inventors did further research and arrived at an intraocular irrigating and enucleated eyeball preservative composition which is disclosed in this specification and claimed.

SUMMARY OF THE INVENTION

This invention relates to an intraocular irrigating and enucleated eyeball preservative composition containing a phosphoric acid diester compound of the following formula or a pharmacologically acceptable salt thereof (hereinafter referred to as the present compound)

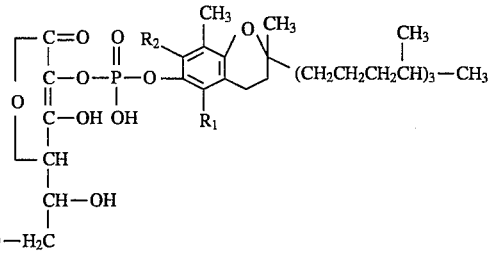

(wherein $R_1$ and $R_2$ are the same or different and each represents a hydrogen atom or a methyl group).

DETAILED DESCRIPTION OF THE INVENTION

Figure 1:
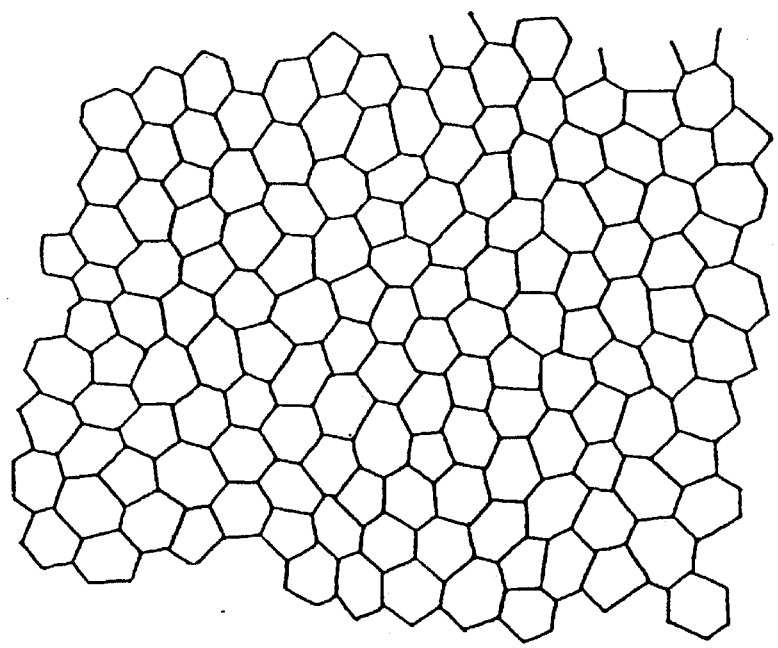
FIG. 1 is the tracing of a scanning electron microphotograph of corneal endothelial cells after the use of the composition of this invention in Experimental Example 1.

The present compound to be used in the intraocular irrigating and enucleated eyeball preservative composition of this invention can be synthesized by the processes described in or suggested in, inter alia, Japanese Patent (JP) Publication Hei-2-44478 and JP Hei-5-23274.

The present compound for use in the intraocular irrigating and enucleated eyeball preservative composition of this invention is already known to be of value as an anticataract drug, a prophylactic and therapeutic drug for climacteric disturbance, a skin-beautifying cosmetic (JP Publication Hei-2-44478), an anti-inflammatory drug (JP Publication Hei-1-27044), an antiulcer drug (JP Kokai Sho-63-27062) and a prophylactic and therapeutic agent for ischemic disorder in organs (JP Kokai Hei-2-111722), for instance.

However, it has not been known to this day that the present compound is of use as an active ingredient of intraocular irrigating fluids or enucleated eyeball preservative compositions.

The present compound represented by the above formula, either the free acid form or a pharmacologically acceptable salt thereof, can be used for the object of the present invention. The salt may be an alkali metal salt such as the sodium salt and the potassium salt, or an alkaline earth metal salt such as the calcium salt and the magnesium salt.

The intraocular irrigating and enucleated eyeball preservative composition of this invention may contain any one or, if necessary, more than one species of the present compound depending on the intended use and need.

The intraocular irrigating and enucleated eyeball preservative composition of this invention can be provided in a liquid form or in a solid form for extemporaneous reconstitution. The solid composition is preferably dissolved, suspended or emulsified in purified water, physiological saline or the like. The solid composition includes dosage forms such as tablets, granules and powders, all of which can be manufactured by the per se known procedures. Preferably, these preparations are sterilized by known procedures such as filtration through a bacterial filter and autoclaving.

The present compound to be used in the intraocular irrigating and enucleated eyeball preservative composition of this invention is sparingly toxic and, therefore, is safe clinically. It can be put to use with advantage on the occasion of various ophthalmic operations and for the preservation of enucleated eyeballs. [$LD_{50}$ of the sodium salt of phosphoric acid diester of L-ascorbic acid, DL-α-tocopherol (hereinafter referred to briefly as EPC-Na): Per os>10 g/kg (rat), Subcutaneous administration>793 mg/kg (rat)].

The recommended concentration of the present compound in the present composition for intraocular irrigation depends on the species of the compound but is generally in the range of about 0.01 μg/ml to about 200 μg/ml, preferably about 0.5 μg/ml to about 10 μg/ml, as the final concentration.

The dosage of the present compound contained in the composition for the preservation of isolated eyeballs is also dependent on the species of the compound, condition of the eyeball, preservation temperature and required preservation time but is generally about $5\times10^{-9}$ g/ml to $5\times10^{-3}$ g/ml and preferably about $5\times10^{-8}$ g/ml to $5\times10^{-5}$ g/ml as the final concentration.

The pH of a liquid form of the intraocular irrigating and enucleated eyeball preservative composition of this invention is preferably adjusted to about 6.5 to 7.5 by the per se known procedure.

The osmotic pressure ratio of a liquid form of the composition of this invention is preferably controlled at about 0.5 to 3 and, for still better results, about 0.8 to 2 by the per se known procedure. The pH of the liquid is preferably adjusted to about 3 to 10 and, for still better results, about 4 to 9.

For use as an intraocular irrigating composition, the composition of this invention may contain, unless contrary to the object of the invention, various other components which are usually included in intraocular irrigating solutions, e.g. electrolytes such as calcium chloride, magnesium chloride, magnesium sulfate, sodium acetate, sodium phosphate, potassium phosphate, sodium citrate, sodium hydrogen carbonate, e.t.c., monosaccharides such as glucose e.t.c., peptides such as glutathione and glutathione disulfide, and antibiotics such as penicillin G etc. in appropriate amounts.

For use of the composition of this invention as an eyeball preservative composition, the composition may contain, unless contrary to the object of this invention, a variety of other components which are usually incorporated in eyeball preservative products, e.g. nutrients, an isotonizing agent, a pH control agent, preservatives, solubilizers, a rheology modifier, etc., in appropriate amounts. Among such components may be reckoned sugars, salts, amino acids and organic acids. The sugars may be sucrose, glucose, lactose, dextrose, mannitol and so on. The salts include sodium chloride, sodium citrate, sodium phosphate, etc. The amino acids may be glycine, glutamic acid, lysine and so on. The organic acids include citric acid, acetic acid, lactic acid an so on. Unless contrary to the object of the invention, the enucleated eyeball preservative of this invention may further contain other medicinal substances, such as immunosuppressants, antibiotics, therapeutic agents for ischemic diseases, etc., in appropriate amounts.

The proper eyeball preservation temperature with the composition of this invention as an enucleated eyeball preservative is dependent on the species and dosage of the present compound, condition of the eyeball and required preservation time, among other conditions, but is generally about −5° C. to 20° C. and preferably about 0° C. to 15° C.

For use of the composition of this invention as an enucleated eyeball preservative, the enucleated eyeball may be preserved as it is or any tissues of the eyeball, such as the sclerocornea, retina or crystalline lens, may be independently preserved, the choice depending on the intended operation.

In preserving the enucleated eyeball with the composition of this invention, the conventional eyeball preservation container and other hardware can be utilized.

EXAMPLES

The following experimental and working examples are intended to describe the invention in further detail. [Experimental Example 1]Cornea-protecting Effect of the Present Compound In order to evaluate the cornea tissue-protecting effect of L-ascorbyl DL-α-tocopheryl phosphate monopotassium (hereinafter referred to briefly as EPC-K), compositions with and without EPC-K were prepared and their protective effects on endothelial cells were compared using rabbit sclerocorneal sections.

[Test Materials]

The test was performed using the composition containing EPC-K and the composition excluding EPC-K from the like formulation as shown below in Example 1.

[Method]

Six male Japanese white rabbits without ocular abnormalities were used. After sacrifice of the animals, the eyeballs were enucleated and sclerocorneal sections were prepared. Six eyes were assigned to the EPC-K-containing composition and the remaining six eyes to the EPC-K-free composition. The sclerocorneal sections were respectively placed in the wells of a 6-well plate and the test composition was placed in each well. The plate was stored at 4° C. and the composition was replaced with the fresh one on a daily basis. After 7 days, the cornea was fixed and endothelial specimens were prepared for scanning electron microscopy. The endothelium was then photographed and the hexagonal cells were counted to find its percentage.

[Results]

Figure 2:
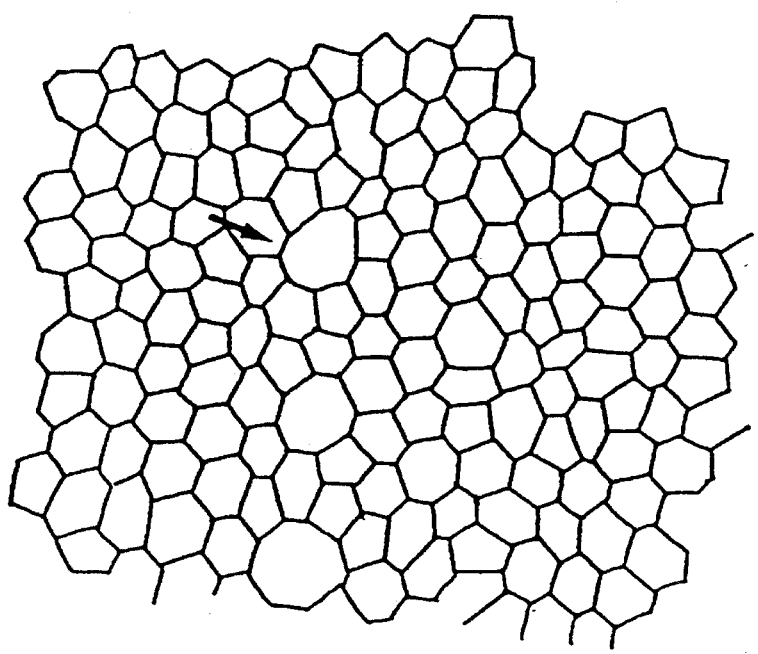
FIG. 2 is the tracing of a scanning electron microphotograph of corneal endothelial cells after the use of the composition excluding the present compound in Experimental Example 1.

As shown in Table 1, microscopic observation revealed that with the formula containing EPC-K, the percentage of hexagonal cells was higher, indicating a greater cornea protecting effect (cf. FIGS. 1 and 2). As clearly seen from FIG. 1, the composition of this invention caused little degeneration of hexagonal cells, with the variation of cell size being also smaller than in the control group. It can also be seen from FIG. 2 that when the composition not containing the present compound was used, normally hexagonal cells underwent degeneration, as epitomized by the cell indicated by the arrowmark in the center, with the prominent appearance of polygonal and giant cells.

TABLE 1

| | Percentage of Hexagonal cells |
|---|---|
| Formulation containing EPC-K | 70.8 ± 3.8* |
| Formulation without EPC-K | 65.5 ± 4.5 |

*Significantly different from the control group ($p < 0.05$).

[Example 1]

According to the following formula, an intraocular irrigating and enucleated eyeball preservative composition is manufactured by the per se known sterile procedure.

| | |
|---|---|
| EPC-K | 70.6 μg |
| Sodium chloride | 0.775 g |
| Potassium chloride | 0.041 g |
| Calcium chloride dihydrate | 0.0172 g |
| Magnesium sulfate heptahydrate | 0.0218 g |
| Sodium dihydrogen phosphate | 0.016 g |
| Disodium monohydrogen phosphate | 0.1031 g |
| Sodium citrate | 0.09 g |
| Glucose | 0.782 g |
| Chondroitin sulfate Na | 2.5 g |
| Penicillin G | 20,000 U |
| Purified water | q.s. |
| Total | 100 ml |
| pH | 7.43 |

[Example 2]

According to the following formula, an intraocular irrigating and enucleated eyeball preservative composition is manufactured by the per se known sterile procedure.

| | |
|---|---|
| EPC-K | 0.1 mg |
| Sodium chloride | 0.66 g |
| Potassium chloride | 0.036 g |
| Potassium chloride dihydrate | 0.018 g |
| Magnesium sulfate heptahydrate | 0.03 g |
| Sodium hydrogen carbonate | 0.25 g |
| Citric acid | 0.08 g |
| Sodium acetate trihydrate | 0.06 g |
| Glucose | 0.15 g |
| Sodium hydroxide | q.s. |
| Hydrochloric acid | q.s. |
| Purified water | q.s. |
| Total | 100 ml |
| pH | 6.6 |

[Example 3]

According to the following formula, a sterile solid composition and a sterile liquid composition are manufactured. The solid composition is extemporaneously dissolved in the liquid composition.

| (1) Liquid composition | |
|---|---|
| Sodium chloride | 0.7 g |
| Calcium chloride | 0.04 g |
| Calcium chloride dihydrate | 0.02 g |
| Magnesium sulfate heptahydrate | 0.03 g |
| Sodium hydrogen carbonate | 0.3 g |
| Citric acid | 0.1 g |
| Sodium acetate trihydrate | 0.1 g |
| Sodium hydroxide | q.s. |
| Hydrochloric acid | q.s. |
| Purified water | q.s. |
| Total | 100 ml |
| pH | 7.3 |
| (2) Solid composition | |
| EPC-K | 1 mg |
| Glucose | 0.15 g |

What is claimed is:

1. A method for protecting cornea tissues from physiological damage during an ophthalmic operation which comprises irrigating such tissues during such operation with an intraocular irrigating composition which comprises an effective amount of a compound of the formula

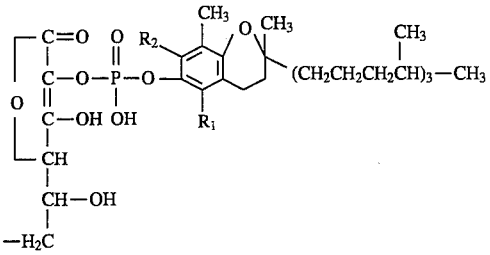

wherein $R_1$ and $R_2$ are the same or different and each represents a hydrogen atom or a methyl group, or a pharmacologically acceptable salt thereof.

2. A method according to claim 1 wherein the compound is L-ascorbyl-DL-α-tocopheryl phosphate monopotassium.

3. A method for preserving the physiological function of an enucleated cornea which comprises storing the enucleated cornea in a preservative composition comprising a physiological function preserving effective amount of a compound of the formula

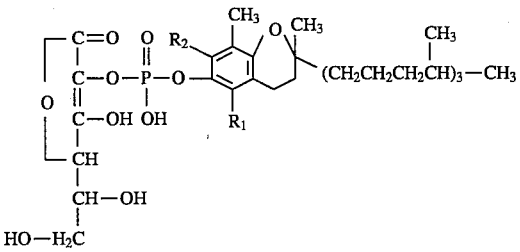

wherein $R_1$ and $R_2$ are the same or different and each represents a hydrogen atom or a methyl group, or a pharmacologically acceptable salt thereof.

4. A method according to claim 3 wherein the compound is L-ascorbyl-DL-α-tocopheryl phosphate monopotassium.

* * * * *